United States Patent [19]

Eriksoo

[11] 4,249,002
[45] Feb. 3, 1981

[54] POLYCYCLIC AMINES AND INTERMEDIATES THEREFOR

[75] Inventor: Edgar Eriksoo, Helsingborg, Sweden

[73] Assignee: Aktiebolaget Leo, Helsingborg, Sweden

[21] Appl. No.: 917,923

[22] Filed: Jun. 22, 1978

Related U.S. Application Data

[62] Division of Ser. No. 703,534, Jul. 8, 1976, abandoned.

[30] Foreign Application Priority Data

Jul. 10, 1975 [GB] United Kingdom ............... 29161/75

[51] Int. Cl.³ ................. C07D 279/22; C07D 223/28; C07D 141/02; A61K 31/55; A61K 31/38
[52] U.S. Cl. .................................. 544/38; 260/458 C; 260/502.6; 260/239 D; 544/380; 549/26; 424/244
[58] Field of Search ............ 260/239 D, 458 C, 502.6; 544/380, 38; 549/26

[56] References Cited

U.S. PATENT DOCUMENTS

| 3,036,064 | 5/1962 | Schindler | 260/239 D |
| 3,159,663 | 12/1964 | Klass et al. | 260/327 R |
| 3,803,238 | 4/1974 | Struve et al. | 260/585 R |

Primary Examiner—Donald G. Daus
Assistant Examiner—D. B. Springer
Attorney, Agent, or Firm—Gordon W. Hueschen

[57] ABSTRACT

This invention relates to a new method for the preparation of amines containing alkylene groups by using cyclic alkylene sulphuric esters, and novel intermediates for use in the method.

The new method is useful for preparation of i.a. pharmaceuticals. The novel intermediates are useful i.a. as surfactants.

13 Claims, No Drawings

POLYCYCLIC AMINES AND INTERMEDIATES THEREFOR

This is a division of application Ser. No. 703,534, filed July 8, 1976, now abandoned.

One aspect of this invention concerns a new method for synthesis of compounds of the general formula (I), $$R—A—R^2 \quad (I)$$

where R is the radical of a compound RH which is characterized by being able to form a reactive nucleophile in form of the corresponding anion $R^\ominus$, where $R^2$ is the radical of a compound $R^2H$ which is characterized by being an amine which is a reactive nucleophile, and where A is an alkylene group optionally symmetrically substituted by one or two groups unreactive under the conditions of the reaction. Said alkylene group has two to four carbon atoms in the carbon chain between R and $R^2$. By the expression "Symmetrically substituted" is meant substitution symmetrical in relation to the terminal atoms of said chain.

Unsubstituted ethylene, trimethylene, and tetramethylene groups are preferred. Preferred substituents are lower alkyl (especially methyl), phenoxy and phenyl. Any benzene ring present in A may be unsubstituted or substituted with groups unreactive under the conditions of the reaction. If the trimethylene group is substituted, monosubstitution is preferred.

If A is a substituted ethylene group preferred substituents are two methyl groups or a tetramethylene group.

According to the present invention the preparation of compounds of the general formula (I) is effected by two consecutive steps with or without isolation of the intermediate compound having the general formula (III) as shown below and produced in the first step of the process.

In the first step a compound of the general formula RM is reacted with a cyclic sulphuric ester of the general formula (II)

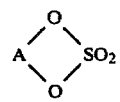

(II)

so that a compound of the general formula (III)

$$R—A—O—SO_2OM \quad (III)$$

is obtained, said compound III being then reacted in the second step with a compound of the general formula $R^2H$ so that a compound of the general formula (I) is obtained, wherein R, $R^2$ and A have the assigned meanings.

RM may be prepared from RH and a compound MB, optionally in situ, where M represents an unreactive cation and B is a basic anion.

The known methods for the preparation of compounds of the general formula $R—A—R^2$ are illustrated by the following schema.

One such method is as follows

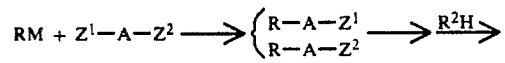

-continued $$R—A—R^2$$

$Z^1$ and $Z^2$ are the same or different and represent halogen atoms (chlorine, bromine or iodine) or alkyl or aryl sulphonyloxy groups. In this reaction the compound $Z^1—A—Z^2$ contains two reactive groups $Z^1$ and $Z^1$ which both are able to react with reactive nucleophiles and which both have about the same order of reactivity also if dissimilar, thus resulting in a mixture of the compounds $R—A—Z^1$ and $R—A—Z^2$ in the first step in the above reaction scheme. The consequence thereof is also that byproducts having the structure $R—A—R$ are formed in the reaction whereby valuable starting materials are irreversibly lost.

Furthermore, the starting materials, the intermediates and the byproducts are neutral molecules and difficult to separate from each other. If the starting material $Z^1—A—Z^2$ is not completely removed before proceeding to the second step a complex mixture of amines is obtained where $Z^1$ and $Z^2$ or both are replaced by $R^2$. The isolation of the desired end product $R—A—R^2$ from such a mixture is complicated and laborious.

Another known method used for the preparation of amines of the general formula $R—A—R^2$ is the following.

$$RM + Z^1—A—R^2 \rightarrow R—A—R^2$$

This method can only be used for the preparation of tertiary amines. Also in this method the starting material $Z^1—A—R^2$ and the end product are amines which complicates the isolation and purification of the end product $R—A—R^2$. Furthermore, the intermediates $Z^1—A—R^2$ are unstable and its preparation presents problems.

The reactions involved in the method of this invention can be depicted by the following reaction scheme

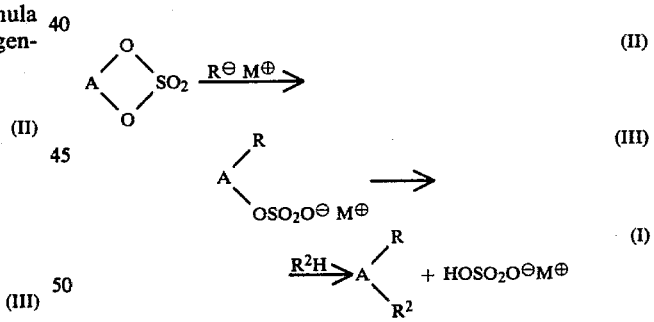

The method of this invention for the preparation of compounds of the general formula (I) is based on the fact that the compounds of the general formula (II) having two identical reactive sites (the two carbon atoms of the ring adjacent to the oxygen atoms), when employed for the alkylation of the starting compound RM, undergo reaction only to the extent of a single reaction site to produce a compound of the general formula (III), which does not further react with additional starting material after it is formed.

The reactivity of compounds of the general formula (II) has been found to be much higher than that of compounds of the general formula (III). Further, the compounds of the general formula (III) have been found to have very low reactivity towards nucleophilic anions being themselves anions. For these reasons the present process can be carried out as consecutive reactions which involves two distinct steps, with or without the isolation of the intermediate of the general formula (III), to give generally good and frequently excellent yields and conversions.

A further advantage is that, in each step, the starting materials on the one hand and the products on the other hand differ sharply in their physico-chemical properties and so can therefore easily be separated, e.g. by a simple partition between an organic and an aqueous phase.

The starting material RM consists of the nucleophilic anion $R^\ominus$ in combination with the unreactive cation $M^\oplus$, and innumerable compounds of this type are known.

References are made to R. Adams et al. (Ed:s), Organic Reactions, vol. 8 (1954) p. 258-304, J. Wiley & Sons Inc.; E. Müller (Ed.) Methoden der Organischen Chemie (Houben-Weyl), Georg Thieme Verlag, Stuttgart, vol. 6/2 (1963) 1-70, vol. 13/1 (1970) 3-85, 93-253 and 255-225, vol. 13/2 (1973) 47-527; Kharash, Reinmuth: Grignard Reactions of Nonmetallic Substances, Prentice-Hall Inc., Englewood Cliffs, N.J., 1954; H. House, Modern Synthetic Reactions 2nd Ed., W. A. Benjamin, Inc. (1972) p. 492-628; for representative starting materials of this type. Alternatively they may be readily prepared in situ, as shown by the foregoing references and as further illustrated and exemplified herein.

The base MB and the type of solvent are normally selected so that they are compatible and in conformity with the acidity of the compound RH used, as well known in the art.

Representative unreactive cations $M^\oplus$ may be the cations of the alkaline metals, Li, Na and K or the cations of the alkaline earth metals Mg and Ca ($M^\oplus = \frac{1}{2}$ $Ca^{2+}$ and $\frac{1}{2}Mg^{2+}$). Other such cations are quaternary ammonium ions and cations, such as $MgCl^+$, $MgBr^+$ and $MgI^+$, formed in the reaction of Grignard compounds with compounds containing active hydrogen atoms. Such cations are well established in the art, as indicated by the foregoing references.

Innumerable compounds of the general formula RH are known and may be of any one of the following three types. It may be a compound capable of forming a reactive carbanion. The compound RH may also be a compound containing an >NH group capable of forming the reactive anion $>N^\ominus$. RH may also be a compound where H is part of an alcoholic or a phenolic hydroxyl group which can form a reactive oxide anion.

The basic anion $B^\ominus$ of MB which is reacted with RH to give RM may illustratively be a hydroxide, alkoxide, amide, hydride or carbonate. It may also be a carbanion which is the reactive part of Grignard compounds and of metalorganic compounds such as phenyllithium and butyllithium.

$R^2H$ is a reactive nucleophilic amine which is ammonia or a primary or secondary amine.

It is preferred that $R^2H$ contains a primary amino group and lower alkyl amines, especially methylamine, are particularly preferred as this reactant.

The starting materials RM and $R^2H$ may be open-chain molecules, or contain alicyclic, aromatic, or heterocyclic rings, having up to maximum of forty carbon atoms inclusive of substituents.

Thus RM is derived from RH which may be exemplified by the following types of compounds: straight or branched alkanes and alkenes such as methane, ethane, propene, n-butane, and neopentane; arenes such as benzene, naphthalene, fluorene, indene, indane, 5H-dibenzo(a,d)cycloheptene, 10,11-dihydro-5H-dibenzo(a,d)cyclohepten; cycloalkanes such as cyclopentane and cyclohexane; arylalkanes such as toluene, ethylbenzene and methylnaphthalenes; diarylalkanes such as diphenylmethane; arylamines such as aniline, p-anisidine, N-methylaniline, and 1- and 2-naphthylamine; diarylamines such as diphenylamine; heterocyclic compounds containing one or more heteroatoms selected from N, O and S, e.g. monocyclic heterocyclic compounds such as furane, thiophene, pyrrol, pyridine, 2-methylpyridine, and 2-pyridone; bicyclic heterocyclic compounds such as indole, quinoline, 2-methylquinoline, isoquinoline, benzimidazole, purine, chromane, and s-triazolo/4,3-a/pyridin-3(2H)-one; tricyclic heterocyclic compounds such as phenothiazine, 5-H-dibenz(b,f)azepine, 10,11-dihydro-5H-dibenz(b,f)azepine, acridine, phenoxazine and carbazole; alkanoles such as methanol, ethanol, isobutanol and n-hexanol; cycloalkanoles such as cyclopentanol, and cyclohexanol; hydroxy-substituted aromatic and heteroaromatic compounds such as phenol, 4-cresol, 1- and 2-naphtol, 2-, 3- and 4-hydroxybiphenyl, 3-pyridinol, and benzohydrol.

The process is preferred for the production of a polycyclic amine included in the above formula $R-A-R^2$ and having the formula

$$R^1-A^1-R^2$$

wherein $R^1$ is the radical of a fused ring system having two of four rings at least one being an aromatic ring, and in addition one of the rings always containing a >CH— or >N— group as a part of that ring only, said ring system having at least eight and not more than twenty carbon atoms, inclusive of substituents, and having not more than four ring-heteroatoms selected from the group consisting of O, S and N; wherein $A^1$ is a symmetrical alkylene group, having a total of two to six carbon atoms, inclusive, which is attached to the ring-nitrogen or ring-carbon atom of said group of $R^1$ and having two to four carbon atoms in the carbon chain between $R^1$ and $R^2$, and wherein $R^2$ is amino or the radical of an amino attached to $A^1$ by an amino-nitrogen atom of said amino and having a maximum of ten carbon atoms, having in addition to said amino-nitrogen atom at most two heteroatoms selected from the group consisting of N and O.

It is especially preferred that $R^1$ above is a tricyclic fused ring system, having at least eight and at most twenty carbon atoms, inclusive of substituents, having at most three ring-heteroatoms selected from the group consisting of O, S, and N, and having at least one aromatic ring and a central ring having the >CH- or >N- groups as part of said central ring only.

It is further preferred that when $R^1$ above is a tricyclic fused ring system it contains two aromatic rings and said central ring. Particularly preferred such ring systems include phenothiazines, 10,11-dihydro-5H-dibenz(b,f)-azepines, 5H-dibenz(b,f)-azepine, and 5H-dibenzo(a,d)cycloheptens, which preferably are at most disubstituted.

Another preferred type of fused ring systems are those where $R^1$ is a bi-cyclic ring system such as indole, indane, indene, quinoline, isoquinoline, benzofuran, benzothiophene, benzimidazole, purine, naphthalene, and chromane, which preferably are at most disubstituted.

In the above formula $R^1-A^1-R^2$ it is preferred that $A^1$ is selected from the group consisting of ethylene, trimethylene, 2-methyl-trimethylene, and tetramethylene.

Primary amines include in $R^2H$ are exemplified by the following types: lower alkylamines such as methylamine, ethylamine, and isopropylamine; alkanolamines such as ethanolamine; cycloalkylamines such as cyclohexylamines; aralkylamines such as benzylamine and 2-phenylethylamine; heterocyclic amines such as 3-aminopyridine and 2-aminothiazole. Lower alkylamines, such as methylamine, are especially preferred.

Secondary amines included in $R^2H$ are exemplified by the following types: lower dialkylamines such as dimethylamine, methyl-ethylamine, and di-n-butylamine; dialkanolamines such diethanolamine; alkyl-aralkylamines such as N-methylbenzylamine; alkyl-cyclohexylamines such as N-methylcyclohexylamine; heterocyclic amines such as pyrrolidine, piperidine, morpholine, lower alkyl derivatives of the foregoing, lower alkylpiperazines, e.g., N-methylpiperazine, hydroxy-lower-alkylpiperazines, e.g., N-(2-hydroxyethyl)-piperazine; aryl-substituted heterocyclic amines such as 4-(3-chlorophenyl)-piperazine, 4-(4-chlorophenyl)-4-hydroxypiperidine, 1-phenyl-1,3,8-triazaspiro(4,5)-decan-4-one, and 1-(4-piperidyl)-benzoimidazolinone. Lower dialkylamines, such as dimethylamine, and amines where the amine-nitrogen atom is a part of a monocyclic ring, are especially preferred when $R^2$ is a part of $R^1-A^1-R^2$.

The types of compounds RH and $R^2H$, mentioned above, may be unsubstituted, or substituted with groups unreactive under the conditions of the reaction.

If either of RH and $R^2H$ contains more than one reactive nucleophilic group, it is preferred that such groups, the participation of which in the reaction is not desired, are protected by suitable protecting groups, such as benzyl, which are readily removed by hydrogenolysis to restore oxygen or nitrogen containing groups, or ester and ether groups, which are readily reconverted to hydroxy with aid of hydrolysis, all as conventional in the art.

The first step of the method of this invention, i.e. the reaction between RM and a cyclic sulphuric acid ester to give III, is suitably carried out in liquid medium, preferably at a temperature between $-80°$ and $200°$ C., and if necessary at superatmospheric pressure. A reaction temperature between room temperature and the boiling point of the reaction mixture is particularly preferred. Non-aqueous solvents are preferred, suitable types being hydrocarbons, halogenated hydrocarbons, ethers, esters, ketones, alcohols, amides, sulfoxides, sulfones and mixtures thereof.

The only requirement for the solvent in this step is that it be non-reactive with the reactants and the reaction products under the conditions of the reaction.

The intermediate compound (III) may be used without isolation or may be isolated using standard procedures and purified if necessary or desired. It may, if desired, also be converted to a salt with a cation different from the original one before proceeding to the next step.

The second step, i.e., the reaction between $R^2H$ and (III), may be performed between room temperature and $250°$ C. and if necessary at superatmospheric pressure.

It is preferably carried out in a liquid medium, optionally in the presence of a catalyst. As catalysts for the reaction barium or calcium ions may be used. Barium and calcium ions are preferably used in an amount approximately equivalent to the amount of the intermediate compound (III).

Suitable types of solvents include water, alcohols, ethers, hydrocarbons, sulfoxides, sulfones and mixture thereof. The only requirement for the solvent in this step is that it be non-reactive with the reactants and the reaction products under the conditions of the reaction.

The cyclic sulphates of the general formula (II) are known compounds and/or can be prepared by known methods as described by E. E. Gilbert "Sulfonation and Related Reactions", Interscience Publishers, 1965, p. 367-71.

Another aspect of this invention relates to novel intermediates useful in the method of this invention. Said intermediates are within the scope of the general structure (III) and have the general formula

$$R^6-A^1-OSO_2OM \qquad (IV)$$

wherein $R^6$ is a tricyclic fused ring system having at least eight and at most twenty carbon atoms, inclusive of substituents, having at most three ring-heteroatoms selected from the group consisting of O, S, and N, and having at least one aromatic ring and a central ring having the $>CH-$ or $>N-$ groups as part of said central ring only; wherein $A^1$ is a symmetrical alkylene group, having a total of two to six carbon atoms inclusive, attached to the nitrogen or carbon atoms of said group of the central ring of $R^6$ and $-OSO_2OM$, and wherein M is a cation selected from the group consisting of alkali metal ions, earth alkaline metal ions, and quaternary ammonium ions.

It is preferred that $R^6$ contains two aromatic rings and said central ring.

It is also preferred that $A^1$ in the formula (IV) above is selected from the group consisting of ethylene, trimethylene, 2-methyl-trimethylene and tetramethylene.

Preferred M in formula (IV) above is selected from alkali metal and alkaline earth metal cations, especially lithium, potassium and sodium ions.

It is preferred that $R^6$ is substituted in the ring system by at most two substituents preferably selected from the group consisting of lower alkyl (especially methyl), lower-alkanoyl, lower alkoxy (especially methoxy), F, Cl, $CF_3$, CN, $SO_2N(CH_3)_2$, and $SO_2CF_3$.

Especially preferred novel intermediates have the general formula

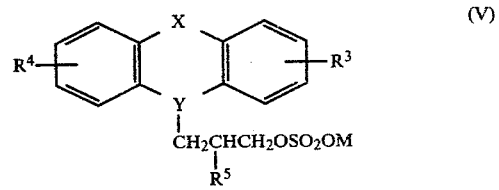

(V)

wherein X is selected from the group consisting of $CH_2CH_2$, $CH=CH$ and S, $CH_2CH_2$ being preferred, wherein Y is N or CH, N being preferred, wherein $R^3$ and $R^4$ are the same or different, and are selected from the group consisting of H, F, Cl, $CF_3$, $OCH_3$, CN, $SO_2N(CH_3)_2$, $SO_2CF_3$, lower alkyl, lower alkanoyl, and lower alkoxy containing at most 4 carbon atoms, hydrogen being preferred, wherein $R^5$ is H or methyl, hydrogen being preferred, and wherein M has the meaning assigned above.

The compounds (IV) are salts of sulphuric monoesters. Being neutral salts, they have physicochemical properties, which make them readily separable from starting materials and end products (I), made therefrom in step two of the process, as described above.

In this disclosure the expression "lower" means that the group referred to contains one to four carbon atoms, inclusive. Thus, lower alkyl, lower alkoxy, and lower alkanoyl include: methyl, ethyl, propyl, iso-propyl, butyl, secondary butyl, iso-butyl, tertiary butyl, methoxy, ethoxy, propoxy, isopropoxy, butoxy, isobutoxy, secondary butoxy, tertiary butoxy, acetyl, propionyl, butyryl, and isobutyryl.

The final products of formula (I) produced according to the method of the present invention find a variety of uses. Those compounds of formula (I) and related compounds are useful pharmaceuticals, having particular application as neuroleptics, antidepressives, and tranquillizers. In addition, the amines of the general formula (I) are reactable in place of other amines for the production of aminoplastic resins, and surface coatings.

In addition, they are convertible by standard reaction procedures into quaternary ammonium salts which have utility as germicides and detergents. Because of their capacity for forming acid addition salts with usual mineral and organic acids, they are useful, particularly the tertiary amines, as acid binding agents for employment in chemical reactions involving the production of acid as one of the reaction products, particularly where the desired reaction product is unstable in the presence of acid.

The compounds of the present invention defined by the general formula (IV) have lipophilic properties and also hydrophilic properties due to the presence therein of a hydrophilic group, and are accordingly useful as surface active agents, and in preparations of the usual type for cosmetic and industrial uses involving such surface active agents. They may be employed in compositions in which surface active agents of the sodium lauryl sulphate type are commonly employed. They are particularly useful as intermediates for the preparation of the corresponding compounds having the formula (I), which are already stated are known pharmaceutical agents having desirable neuroleptic, antidepressive, and tranquillizing activity and utility.

The compounds named in the following examples and being within the scope of the general formulas (I) and (IV) above, are of particular interest for the intended purposes. The examples are intended to illustrate but not to limit the scope of the invention.

EXAMPLE 1

24.4 Parts of 10,11-dihydro-5H-dibenz(b,f)-azepine are dissolved in 200 parts of anhydrous toluene in nitrogen atmosphere and 8.9 parts of sodium amide are added. The reaction mixture is stirred for 7 hours at 80° C. A solution of 17.3 parts of trimethylenesulphate in 150 parts of anhydrous toluene is added and stirring is continued for 6 hours at 80° C. during which time the sodium salt of 3-(10,11-dihydro-5H-dibenz(b,f)-azepin-5-yl)-propyl sulphate (novel intermediate (IV)) precipitates. The reaction mixture is cooled to room temperature and 50 parts of water added. The above mentioned precipitated sodium salt is filtered off and transferred to an autoclave furnished with stirrer and 150 parts of 33% aqueous methylamine solution are added. The reaction mixture is heated at 150° C. for 6 hours and then cooled to room temperature. The excess of methylamine is evaporated and the reaction mixture is acidified with hydrochloric acid and washed with toluene. The aqueous phase is then extracted with $2 \times 100$ parts of methylene chloride and the extract is dried over anhydrous sodium sulphate. The dried solution is evaporated to dryness. The residue is crystallized from butanone, and 28.3 parts of 10,11-dihydro-5-/3-(methylamino)-propyl/-5H-dibenz(b,f)azepine hydrochloride are obtained, m.p. 215°–17° C.

By repeating the above procedure but substituting dimethylamine for methylamine, 10,11-dihydro-5-/3-(dimethylamino)-propyl/-5H-dibenz(b,f)-azepine hydrochloride, m.p. 173°–4° C., is obtained.

If ammonia is substituted for methylamine, 10,11-dihydro-5-(3-aminopropyl)-5H-dibenz(b,f)-azepine hydrochloride, m.p. 274°–7° C., is obtained.

By an analogous procedure the following compounds are prepared.

3-chloro-10,11-dihydro-5-/3-(dimethylamino)-propyl/-5H-dibenz(b,f)-azepine hydrochloride, m.p. 188°–90° C., and 3-chloro-10,11-dihydro-5-/3-(methylamino)-propyl/-5H-dibenz(b,f)-azepine hydrochloride, m.p. 212°–15° C., via 3-(3chloro-10,11-dihydro-5H-dibenz(b,f)azepin-5-yl)-propyl sulphate sodium salt (IV) by using dimethylamine and methylamine, respectively.

5-/3-(dimethylamino)-propyl/-5H-dibenz(b,f)azepine hydrochloride, m.p. 175°–7° C., and 5-/3-(methylamino)-propyl/-5H-dibenz(b,f)azepine hydrochloride, m.p. 205°–6° C., via 3-(5H-dibenz(b,f)azepin-5-yl)-propyl sulphate sodium salt (IV) by using dimethylamine and methylamine, respectively.

10,11-dihydro-5-[4-(dimethyl amino)-butyl]-5H-dibenz(b,f)azepine (b.p. 180° C./0.1) via 4-[10,11-dihydro-5H-dibenz(b,f)azepin-5-yl]-butyl sulphate sodium salt which is obtained as above from 10,11-dihydro-5H-dibenz(b,f)azepine and tetramethylene sulphate.

EXAMPLE 2

23 Parts of 2-chlorophenothiazine are dissolved in 200 parts of anhydrous toluene in nitrogen atmosphere and 5 parts of sodium amide are added. The reaction mixture is stirred at 110° C. for 16 hours and then cooled down to room temperature. A solution of 13.8 parts of trimethylenesulphate in 100 parts of anhydrous toluene is added during 15 minutes and stirring is continued at 80° C. for 2 hours and then cooled to room temperature and 100 parts of water are carefully added. The aqueous phase is separated and evaporated to dryness in vacuo and crude 3-(2-chlorophenothiazin-10-yl)-propyl sulphate sodium salt (IV) is obtained as a residue.

The residue is dissolved in 150 parts of a 40% aqueous solution of dimethylamine and heated in an autoclave at 140° C. for 16 hours and then cooled to room temperature. The excess of methylamine is evaporated and the reaction mixture is acidified with hydrochloric acid and washed with toluene. The aqueous phase is then extracted with $2 \times 100$ parts of methylene chloride. The extract is dried over anhydrous sodium sulphate and the dried solution is evaporated to dryness in vacuo. The residue is crystallized from butanone and 2-chloro-10-(3-dimethylaminopropyl)-phenothiazine hydrochloride is obtained, m.p. 178°–80° C. (Dec.).

If methylamine is substituted for dimethylamine 2-chloro-10-(3-methylaminopropyl)-phenothiazine hydrochloride, m.p. 185°–7° C., is obtained.

By an analogous procedure the following compounds are prepared.

2-trifluoromethyl-10-(3-dimethylaminopropyl)-phenothiazine (hydrochloride, m.p. 172°-4° C.) via 3-(2-trifluoromethylphenothiazine-10-yl)-propyl sulphate sodium salt (IV).

2-cyano-10-/3-(4-hydroxypiperidino)-propyl/phenothiazine (m.p. 115°-17° C.) via 3-(2-cyanophenothiazin-10-yl)-propyl sulphate sodium salt (IV).

2-acetyl-10-(3-dimethylaminopropyl)-phenothiazine (maleate, m.p. 134°6° C.) via 3-(2-acetylphenothiazin-10-yl)-propyl sulphate sodium salt (IV).

2-butyryl-10-/3-(4-methyl-1-piperazinyl)-propyl/-phenothiazine (maleate, m.p. 180°-2° C.) via 3-(2-butyrylphenothiazin-10-yl)-propyl sulphate sodium salt (IV and N-methylpiperazine.

2-methoxy-10-(3-dimethylaminopropyl)-phenothiazine (base, m.p. 44°-6° C.) via 3-(2-methoxyphenothiazine-10-yl)-propyl sulphate sodium salt (IV).

2-trifluoromethyl-7-fluoro-10-/3-(4-(2-hydroxyethyl)-piperazine-1-yl)propyl/phenothiazine (base, m.p. 218°-20° C.) via 3-(2-trifluoromethyl-7-fluoro-phenothiazin-10-yl)-propyl sulphate sodium salt (IV).

2-chloro-10-(4-dimethylamino-butyl)-phenothiazine hydrochloride, m.p. 160°-2° (via 4-(2-chlorophenothiazin-10-yl)-butyl sulphate sodium salt which is prepared as above from 2-chloro-phenothiazine and tetramethylene sulphate.

1-(3-dimethylaminopropyl)-indole(hydrochloride, m.p. 150°-2° C.) via 3-(indol-1-yl)-propyl sulphate sodium salt.

EXAMPLE 3

3.9 Parts of sodium amide are added to a solution of 19 parts of 5H-dibenzo(a,d)cyclohepten in 50 parts of hexamethyl phosphoric triamide and the mixture is stirred over night at room temperature, thereafter 13.8 parts of trimethylenesulphate are added. 400 Parts of anhydrous ethyl ether are added and the precipitated 3-(5H-dibenzo(a,d)-cycloheptene-5-yl)-propyl sulphate sodium salt (IV) is filtered off and together with 120 parts of 40% aqueous methylamine autoclaved at 150° C. for 8 hours and then cooled to room temperature. The excess of methylene is evaporated and the reaction mixture is acidified with hydrochloric acid and washed with toluene. The aqueous phase is then extracted with 2×100 parts of methylene chloride. The extract is dried over anhydrous sodium sulphate and the dried solution is evaporated to dryness in vacuo. The residue is crystallized from methylisobutylketone and N-methyl-5H-dibenzo(a,d)cyclohepten-5-propylamine hydrochloride, m.p. 169°-71° C., is obtained.

The following compound are prepared by an analogous procedure 10,11-dihydro-5-(3-dimethylamino-2-methylpropyl)-5H-dibenz(b,f)-azepine (hydrochloride, m.p. 188°-90° C.) via 3-(10,11-dihydro-5H-dibenz(b,f)azepin-5-yl)-2-methylpropyl sulphate sodium salt (IV).

1-(3-dimethylaminopropyl)-3-phenyl-indene (b.p. 150°-5° C./0.3) via 3-(3-phenylinden-1-yl)-propyl sulphate sodium salt.

EXAMPLE 4

18.4 Parts of benzohydrol are dissolved in 100 parts of 1,2-dimethoxyethane and 2.4 parts of sodium hydride are added while stirring at room temperature. The mixture is then refluxed for 4 hours and cooled to room temperature and a solution of 13.8 parts of trimethylenesulphate in 100 parts of 1,2-dimethoxyethane is added so that the temperature of the reaction mixture does not exceed 50° C. The reaction mixture is then refluxed for one hour and the reaction mixture is evaporated to dryness in vacuo. Water (100 parts) and ethyl ether (200 parts) are added to the residue. The phases are separated after shaking and the aqueous phase is evaporated to dryness, and the residue obtained consists of crude 3-(diphenylmethoxy)-propyl sulphate sodium salt.

150 Parts of 40% aqueous dimethylamine solution are added to the residue and the mixture obtained is autoclaved at 155° C. for 6 hours. The excess of methylamine is evaporated and the reaction mixture is acidified with hydrochloric acid and washed with toluene. The aqueous phase is then extracted with 2×100 parts of methylene chloride. The extract is dried over anhydrous sodium sulphate and the dried solution is evaporated to dryness in vacuo. The residue is crystallized and N,N-dimethyl-3-(diphenylmethoxy)-propylamine hydrochloride, m.p. 109°-71° C., is obtained.

If methylamine is substituted for dimethylamine, N-methyl-3-(diphenyl-methoxy)-propylamine hydrochloride is obtained, m.p. 160°-2° C.

The following compounds are prepared by an analogous procedure 3-cyclohexyloxypropylamine (b.p. 117°/20°) via 3-cyclohexyloxypropyl sulphate sodium salt.

3-benzyloxypropylamine (b.p. 99°-100°/1) via 3-benzyloxypropyl sulphate sodium salt.

EXAMPLE 5

130 Parts of sodium 4-cresylate (prepared from 108 parts of 4-cresol and 40 parts of sodium hydroxide in 200 parts of methanol and evaporation to dryness) are suspended in 400 parts of anhydrous toluene and 138 parts of trimethylenesulphate are added in portions so that the temperature of the reaction mixture does not exceed 50° C. Stirring is continued at 50° C. for one hour and the reaction mixture is left at room temperature over night. The precipitate formed is filtered off and recrystallized from methanol.

To the 3-(4-methylphenyl)-propyl sulphate sodium salt so obtained are added 200 parts of N-methylpiperazine and refluxed and stirred for two hours. The reaction mixture is cooled to room temperature. Water and ethyl ether are added. The ethereal phase is washed with water and dried. The extract is evaporated to dryness in vacuo and the residue crystallizes and N-methyl-N-3-(4-methyl-phenoxy)-propyl-piperazine, m.p. 45°-7° C., is obtained.

EXAMPLE 6

181 Parts of bromobenzene and 26 parts of magnesium are converted to the Grignard compound in 1000 parts of ethyl ether. A solution of 138 parts of trimethylene sulphate in 500 parts of ethyl ether is added. The reaction mixture is refluxed for 6 hours. The precipitate formed is filtered off and placed in autoclave with 1000 parts of a 40% solution of methylamine and heated at 155° C. for 4 hours and thereafter worked up as in Example 1.

N-methyl-3-phenylpropylamine hydrochloride is obtained, m.p. 145°-6° C.

When the same intermediate sulphate salt as above is reacted with benzylamine, N-benzyl-1-phenyl-propylamine (hydrochloride, m.p. 258°-60° C.) is obtained.

By an analogous procedure 3-(2-aminoethyl)-benzothiophene (b.p. 125° C./1) is obtained via 2-(benzothiophen-3-yl)ethyl sulphate bromomagnesium salt and treatment with ammonia.

By a procedure analogous to that given above phenyllithium is first treated with ethylene sulphate and thereafter with an aqueous solution of dimethylamine and N,N-dimethyl-2-phenylethylamine hydrochloride is obtained, m.p. 163°–5° C.

EXAMPLE 7

16.8 Parts of diphenylmethane are added to a solution of 6.4 parts of butyllithium in 200 parts of ethyl ether. The reaction mixture is stirred at room temperature for 2 hours whereafter a solution of 13.8 parts of trimethylenesulphate in 100 parts of anhydrous ether are added, whereafter the reaction mixture is refluxed for 2 hours. 100 Parts of water is added and after shaking the aqueous phase is separated and evaporated to dryness in vacuo. 150 Parts of 40% aqueous dimethylamine solution are added to the residue and the reaction mixture is heated at 150° C. for 6 hours and thereafter worked up as in Example 1.

N,N-dimethyl-4,4-diphenyl-butylamine hydrochloride, m.p. 152°–4° C., is obtained.

In an analogous way the following compounds are prepared

N-methyl-4,4-diphenyl-butylamine hydrochloride, m.p. 160°–1° C.

N,N-dimethyl-3,3-diphenyl-propylamine hydrochloride, m.p. 169°–71° C.

N-methyl-3,3-diphenyl-propylamine hydrochloride, m.p. 159°–61° C.

By a procedure analogous to that given above ethylene sulphate is reacted with butyllithium to give n-hexyl sulphate lithium salt which with cyclohexylamine gives N-cyclohexyl-n-hexylamine (b.p. 66° C./0.6).

EXAMPLE 8

12.5 Parts of thionyl chloride are slowly added to a boiling solution of 15.2 parts of 2-phenyl-1,3-propanediol in 30 parts of methylene chloride. The reaction mixture is refluxed for 30 minutes and then distilled in vacuo and 2-phenyltrimethylensulfite (b.p. 136°–40° C./3.5) is collected.

9.5 Parts of 2-phenyl-trimethylenesulfite are dissolved in 20 parts of methylene chloride and added while stirring to a mixture consisting of 7.9 parts of potassium permanganate, 40 parts of water, 25 parts of methylene chloride and 0.1 parts of tetrabutylammonium hydrogen sulphate, while the temperature is kept between 25° and 35° C. Stirring is continued for 15 minutes and the reaction mixture is filtered. The filtrate is decolorized with sodium hydrogen sulphite and separated. The organic phase is dried over anhydrous sodium sulphate and evaporated to dryness in vacuo. The residue consists of 2-phenyl-trimethylene sulphate (m.p. 79°–81° C.).

2-phenyltrimethylensulphate is then converted to 2,3-diphenylpropyl sulphate lithium salt by a procedure analogous to that in Example 6 (with phenyllithium). The lithium salt so obtained is heated in an autoclave at 150° C. for 8 hours with concentrated aqueous ammonia to give 2,3-diphenylpropylamine (hydrochloride, m.p. 188°–90° C.).

By an analogous procedure N,N-dimethyl-3-phenyl-2-phenoxypropylamine is obtained from 2-phenoxytrimethylenesulphate being first reacted with phenylmagnesiumbromide and the intermediate sulphate salt so obtained treated with dimethylamine as above.

Similarly, when 2-methyl-1,3-propanediol is substituted for 2-phenyl-1,3-propanediol in the procedure described above, 2,N,N-trimethyl-3-phenyl-propylamine (hydrochloride, m.p. 90° C.) is obtained.

EXAMPLE 9

A mixture of 100 parts of the sodium salt of 3-(10,11-dihydro-5H-dibenz(b,f)azepin-5-yl)-propyl sulphate, 300 parts of 33% aqueous methyl amine, and 69 parts of barium chloride dihydrate (wherein the barium salt of 3-[10,11-dihydro-5H-dibenz(b,f)azepin-5-yl]-propyl sulphate precipitates) is stirred in an autoclave at 100° C. for 6 hours and the excess of methyl amine is evaporated. The mixture is acidified with hydrochloric acid and barium sulphate is filtered off. The filtrate is processed as in example 1 and 58 parts of 10,11-dihydro-5-[3-(methylamino)-propyl]-5H-dibenz[b,f]azepine hydrochloride are obtained.

I claim:
1. Product of the formula

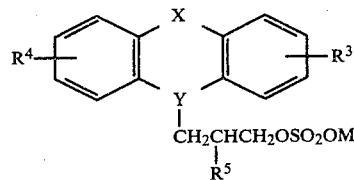

$$CH_2CHCH_2OSO_2OM$$
$$\quad\quad\;\;|$$
$$\quad\quad R^5$$

wherein X is selected from the group consisting of $CH_2CH_2$, $CH=CH$ and S,
wherein Y is N or CH,
wherein $R^3$ and $R^4$ are the same or different, and are selected from the group consisting of H, F, Cl, $CF_3$, CN, $SO_2N(CH_3)_2$, $SO_2CF_3$, and lower alkyl, lower alkanoyl, and lower alkoxy, containing at most four carbon atoms,
wherein $R^5$ is H or methyl, and M is an alkali or alkalineearth metal cation.

2. Product of claim 1, wherein M is an alkali metal cation.
3. Product of claim 1, wherein M is selected from the group consisting of lithium, potassium and sodium ions.
4. Product of claim 1, wherein lower alkyl is methyl and lower alkoxy is $OCH_3$.
5. Product of claim 1, wherein X is $CH_2CH_2$.
6. Product of claim 1, wherein Y is N.
7. Product of claim 1, wherein $R^4=R^5=H$.
8. Product of claim 1 which is 3-(10,11-dihydro-5H-dibenz(b,f)azepin-5-yl)-propyl sulphate, as a salt with M.
9. Product of claim 8 which is 3-(10,11-dihydro-5H-dibenz-(b,f)azepin-5-yl)-propyl sulphate, barium salt.
10. Product of claim 8 which is 3-(10,11-dihydro-5H-dibenz(b,f)azepin-5-yl)-propyl sulphate, sodium salt.
11. Product of claim 1 which is 3-(2-chlorophenothiazin-10-yl)-propyl sulphate, as a salt with M.
12. Product of claim 1 which is 3-(3-chloro-10,11-dihydro-5H-dibenz(b,f)azepin-5-yl)-propyl sulphate, as a salt with M.
13. Product of claim 1 which is 3-(5H-dibenz(b,f)azepin-5-yl)-propyl sulphate, as a salt with M.

* * * * *

UNITED STATES PATENT AND TRADEMARK OFFICE
CERTIFICATE OF CORRECTION

PATENT NO. : 4,249,002

DATED : February 3, 1981

INVENTOR(S) : Edgar Eriksoo

It is certified that error appears in the above—identified patent and that said Letters Patent is hereby corrected as shown below:

Col. 1, the formula at the bottom and Col. 2, line 1, the continued formula at the top; should read as one complete formula;

Col. 2, line 7; "$Z^1$" (third occurrence) should read -- $Z^2$ --
Col. 4, line 32; "of" should read -- to --
Col. 5, line 5; "include" should read -- included --
Col. 6, line 29; "atoms" should read -- atom --
Col. 7, line 43; "are" (first occurrence) should read -- as --
Col. 9, line 44; "methylene" should read -- methylamine --
Col. 9, line 53; "compound" should read -- compounds --

UNITED STATES PATENT AND TRADEMARK OFFICE
CERTIFICATE OF CORRECTION

PATENT NO. : 4,249,002
DATED : February 3, 1981
INVENTOR(S) : Edgar Eriksoo

It is certified that error appears in the above—identified patent and that said Letters Patent is hereby corrected as shown below:

Col. 2, line 13 and line 17 (both occurrences); "byproducts" should read
 -- by-products --
Col. 3, line 20; "255-225," should read -- 255-725, --
Col. 9, line 16; "(IV and" should read -- (IV) and --
Col. 11, line 42; "2-phenyltrimethylensulfite" should read
 -- 2-phenyltrimethylenesulfite --
Col. 11, line 57; "2-phenyltrimethylensulphate" should read
 -- 2-phenyltrimethylenesulphate --

Signed and Sealed this

Seventeenth Day of November 1981

[SEAL]

Attest:

GERALD J. MOSSINGHOFF

Attesting Officer    Commissioner of Patents and Trademarks